United States Patent [19]
Nishiguchi et al.

[11] Patent Number: 4,955,901
[45] Date of Patent: Sep. 11, 1990

[54] INTRAOCULAR IMPLANT HAVING COATING LAYER

[75] Inventors: Toshiji Nishiguchi, Kawasaki; Moriyuki Okamura, Sagamihara; Ikuo Nakajima, Tokyo, all of Japan

[73] Assignee: Canon Kabushiki Kaisha, Tokyo, Japan

[21] Appl. No.: 357,783

[22] Filed: May 30, 1989

[30] Foreign Application Priority Data

May 31, 1988 [JP] Japan ............................ 63-133156

[51] Int. Cl.$^5$ .......................... A61F 2/16; A01N 1.02; B05D 3/06
[52] U.S. Cl. .................................. 623/6; 427/2; 427/37; 427/40; 427/41; 623/901
[58] Field of Search ................. 623/6, 5, 901; 427/2, 427/34, 37, 40, 41

[56] References Cited

U.S. PATENT DOCUMENTS

| | | | |
|---|---|---|---|
| 4,312,575 | 1/1982 | Peyman et al. | 427/41 X |
| 4,731,078 | 3/1988 | Sfoy et al. | 623/6 |
| 4,731,080 | 3/1988 | Galin | 623/6 |
| 4,806,382 | 2/1989 | Goldberg et al. | 623/6 X |
| 4,822,359 | 4/1989 | Tano et al. | 623/6 |

FOREIGN PATENT DOCUMENTS 0034518  2/1982  Japan ................................ 623/6

Primary Examiner—Ronald Frinks
Attorney, Agent, or Firm—Fitzpatrick, Cella Harper & Scinto

[57] ABSTRACT

An intraocular implant comprises a lens substrate having on the surface thereof a coating layer, the coating layer being comprised of a specific compound.

6 Claims, 1 Drawing Sheet

1

INTRAOCULAR IMPLANT HAVING COATING LAYER

BACKGROUND OF THE INVENTION

1. Field of the Invention

The present invention relates to an intraocular implant (or artificial substitute lens) having on its surface a coating layer.

2. Related Background Art

Cataracts have been hitherto treated by surgery to deliver a lens having turned opaque and insert an artificial lens into the lenticular capsule, and recovering vision after the surgery. At present, such an intraocular implant is prevailingly used in the "in-the-bag system" which is considered to cause less complication that may accompany implantation, i.e., a system in which the intraocular implant is inserted into the "lenticular capsule".

As materials for such intraocular implants, polymethyl methacrylate is mainly used, and on the other hand, as materials for a lens support member called "haptic", polymethyl methacrylate, polyvinylidene fluoride or the like is used.

The surfaces of intraocular implants are required to be hydrophilic in order to prevent corneal cells from being damaged or improve a lens fitted feeling, and methods hitherto known as means for making the surfaces of intraocular implants hydrophilic include a method in which the surface of an intraocular implant is subjected to a plasma treatment, or a method in which a hydrophilic coating is formed on the surface of an intraocular implant by plasma polymerization using monomers of a nitro compound represented by the general formula $R-NO_2$ (R is a hydrocarbon).

The method in which the surface of an intraocular implant is subjected to a plasma treatment, which is a method comprising exposing the surface of an intraocular implant to oxygen plasma or nitrogen plasma to make its surface hydrophilic, has the following disadvantage. That is to say, the plasma treatment can achieve a uniform surface treatment with difficulty, and also may cause a deterioration with time wherein the hydrophilic nature becomes poor as time lapses. Hence, this method is not suited for the surface treatment& of intraocular implants which are required to be fitted for a long time.

The coating or film formed by plasma polymerization of the $R-NO_2$ monomers can retain a superior hydrophilic nature, but a small discharge output applied in carrying out the polymerization may bring about an insufficient cross-linkage of the coating formed, resulting in an water-soluble film. Accordingly, a high discharge output is required for the formation of a non-water soluble film, and this necessarily limits film formation conditions to a such w high discharge output may also cause a slight opaqueness on the surface of the intraocular implant narrower scope. The film formation carried out at because of the plasma, which is unsuitable for the intraocular implant.

Other methods for making the surfaces of intraocular implants hydrophilic include dipping and graft polymerization utilizing ultraviolet rays, both of which, however, are accompanied with deterioration with time, and there has been a problem in stability.

On the other hand, the surfaces of intraocular implants are required to be capable of absorbing ultraviolet rays, harmful to retinas. For this purpose, U.S. Pat. No. 4,312,575, for example, discloses that a coloring substance may be included into the intraocular implant so that this coloring substance can absorb ultraviolet rays.

However inclusion of the ultraviolet absorbing substance into an intraocular implant lens substrate has caused the problem that the mechanical strength of the intraocular implant is lowered.

SUMMARY OF THE INVENTION

An object of the present invention is to provide an intraocular implant that may suffer less deterioration with time, of the hydrophilic nature, has a coating laYer capable of being formed under mild film formation conditions for film formation, and can absorb ultraviolet rays without lowering the mechanical strength of the lens.

The intraocular implant of the present invention comprises a lens substrate having on the surface thereof a coating layer, wherein said coating layer is comprised of at least one compound selected from the group consisting of;

an amino compound represented by the general formula: $R_1-NH_2$, wherein $R_1$ represents a hydrocarbon group having not more than 10 carbon atoms;

a cyan compound represented by the general formula: $R_2-CN$, wherein $R_2$ represents a hydrocarbon group having not more than 10 carbon atoms;

an azo compound represented by the general formula: $R_3-N=N-R_4$, wherein $R_3$ and $R_4$ each represent hydrocarbon group having not more than 10 carbon atoms in total or hydrogen atom; and an amino acid represented by the general formula: $R_5-CH(NH_2)COOH$, wherein $R_5$ represents a substituent constituted of C, H or N.

DETAILED DESCRIPTION OF THE PREFERRED EMBODIMENTS

Figure 1:
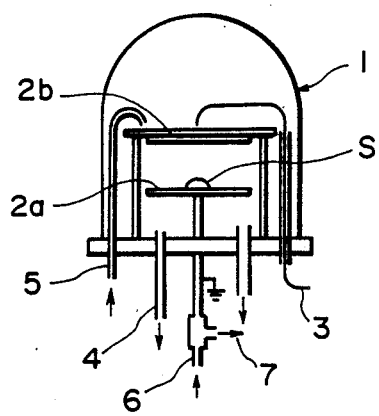
FIG. 1 is a side elevation to show an example of a plasma polymerization apparatus of an internal electrode type, used in preparing the intraocular implant of the present invention.

The intraocular implant of the present invention comprises a lens substrate having on the surface thereof a coating layer which is hydrophilic and capable of absorbing ultraviolet rays. As the lens substrate, conventionally knoWn intraocular implants can be used as they are. Materials preferably used for the lens substrate include, for example, polymethyl methacrylate, hydroxyethyl methacrylate, silicone resins, and polyurethane resins.

Materials used for the coating layer of the intraocular implant of the present invention include an amino compound represented by the general formula: $R_1-NH_2$, wherein $R_1$ represents a hydrocarbon group having not more than 10 carbon atoms; a cyan compound represented by the general formula: $R_2-CN$, wherein $R_2$ represents a hydrocarbon group having not more than 10 carbon atoms; an azo compound represented by the general formula: $R_3-N=N-R_4$, wherein $R_3$ and $R_4$ each represent hydrocarbon group having not more than 10 carbon atoms in total or hydrogen atom; and an amino acid represented by the general formula: $R_5-CH(NH_2)COOH$, wherein $R_5$ represents a substituent constituted of C, H or N.

The above compounds can be free of any deterioration With time, of the hydrophilic nature and yet absorb ultraviolet rays.

The amino compound represented by the general formula: $R_1-NH_2$ includes, for example, saturated or unsaturated aliphatic amino compounds such as aminomethane, aminoethane, 1-aminopropane, 2-aminopropane, 1-aminobutane, 2-aminobutane, 1-amino-2-methylpropane, 1-aminopentane, 1-aminohexane, 1-aminoheptane, 1-aminooctane, 1-aminononane, 1-aminodecane, aminoethylene, 1-aminopropene and 1-aminobutene; saturated or unsaturated alicyclic amino compounds such as aminocyclopentane, aminocyclohexane, aminocycloheptane, aminocyclooctane, aminocyclononane, aminocyclodecane, 1-aminocyclooctene, 1-aminocyclononene, (aminomethyl)cyclohexane and (aminomethyl)cycloheptane; and aromatic amino compounds such as aniline, o-aminotoluene, m-aminotoluene, p-aminotoluene, o-aminostyrene, (aminomethyl)benzene, o-(aminomethyl)toluene, 2-aminop-xylene, 1-aminonaphthalene and 2-aminonaphthalene.

The cyan compound represented by the general formula: $R_2-CN$ includes, for example, saturated or unsaturated aliphatic cyano compounds such as cyanomethane, cyanoethane, cyanopropane, cyanobutane, 1-cyanopropane, 2-cyanopropane, 1-cyanobutane, 2-cyanobutane, 1-cyano-2-methylpropane, 1-cyanopentane, 1-cyanohexane, 1-cyanonheptane, 1-cyanooctane, cyanononane, 1-cyanodecane, cyanoethylene, 1-cyanopropene and 1-cyanobutene; saturated or unsaturated alicyclic cyan compounds such as cyanocyclopentane, cyanocylohexane, cyanocyloheptane, cyanocylooctane, cyanocylononane, cyanocylodecane, 1-cyanocylooctene, 1-cyanocylononene, (cyanomethyl)cyclohexane and (cyanomethyl)cycloheptane; and aromatic cyan compounds such as benzonitrile, o-cyanotoluene, m-cyanotoluene, p-cyanotoluene, o-cyanostyrene, (cyanomethyl)benzene, o-(cyanomethyl)toluene, 2-cyano-p-xylene, 1-cyanonaphthalene and 2-cyanonaphthalene. formula: $R_3-N=N-R_4$ include, for example, both $R_3$ and $R_4$ saturated or unsaturated aliphatic azo compounds such as azomethane, azoethane, azopropane, azopentane, methaneazoethane, methaneazopropane, methaneazobutane, methaneazopentane, ethaneazopropane, ethaneazobutane, azoethylene, azopropylene, methneazoethylene, methneazopropylene and 2-methylpropaneazoethylene; both $R_3$ and $R_4$ saturated or unsaturated alicyclic azo compounds such as azocyclopropane, azocyclobutane, and cyclopropane; both $R_3$ and $R_4$ aromatic azo compounds such as azobenzene, azotoluene, azoxylene, p-aminoazobenzene and p-cyanazobenzene; $R_3$ saturated or unsaturated aliphatic and $R_4$ saturated or unsaturated alicyclic azo compounds such as methaneazocyclopropane, ethaneazocyclobutane, ethyleneazocyclopropane and propyleneazocyclopropane; $R_3$ saturated or unsaturated aliphatic and $R_4$ aromatic azo compounds such as methaneazobenzene, ethaneazoxylene and ethyleneazostyrene; and $R_3$ alicyclic and $R_4$ aromatic azo compounds such as cyclopropaneazobenzene, cyclopenteneazoxylene and cyclopropeneazotoluene.

The amino acid represented by the general formula: $R_5-CH(NH_2)COOH$ include, for example, aliphatic amino acids such as glycine, alanine, valine, serine and asparagine; amino acids having an aromatic ring, such as phenylalanine; and amino acids having a heterocyclic ring, such as histidine.

In the present invention, the above compounds can be used alone or in combination of two or more kinds. A carbon atom number of more than 11 in total, contained in $R_3$ and $R_4$, or a carbon atom number of more than 11 in each of $R_1$ and $R_2$ may result in an insufficient hydrophilic nature of the resulting coating.

The coating layer comprising the above compound(s) has a higher cross-link density and better barrier properties than those of the lens substrate, so that the free monomers contained in the lens substrate can be prevented from dissolving therefrom into an eye. Of the above compounds, the amino acids are particularly preferred because of their superior compatibility with organisms.

The coating layer of the present invention is formed by plasma polymerization or vacuum deposition polymerization using monomers of the above compound(s).

Figure 2:
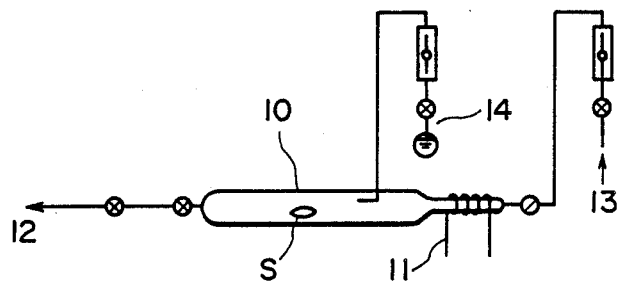
FIG. 2 is a side elevation to show an example of a plasma polymerization apparatus of a non-electrode type, used in preparing the intraocular implant of the present invention.

The plasma polymerization in the present invention can be carried out, for example, by using the apparatus as illustrated in FIG. 1 or 2, but the apparatus are by no means limited to these and any commonly available plasma polymerization apparatus can be used without difficulty.

In the apparatus of an internal electrode type as illustrated in FIG. 1, a pair of electrodes 2a and 2b opposed each other are provided in a reaction vessel 1, and a lens substrate S is placed between them. The electrode 2b is connected to an electric source through a lead wire 3. The inside of the reaction vessel 1 is evacuated through an exhaust vent 4 to which a vacuum pump is connected, and monomers are fed from a monomer feed pipe 5. Film formation is carried out by generating plasma between the electrodes 2a and 2b, where, for example, the temperature of the lens substrate S can be controlled by feeding a cooling water from an inlet 6 and discharging it from an outlet 7 in instances in Which the lens substrate S is placed on the lower electrode 2a.

Plasma polymerization conditions in this instance may be arbitrarily selected based on conditions employed in ordinary plasma polymerization reactions. For example, the inside of the reaction vessel is evacuated to a vacuum of $1 \times 10^{-3}$ Torr, and thereafter monomers are introduced into the reaction vessel 1 at a flow rate of not more than 100 SCCM, and preferably not more than 20 SCCM, per minute, and the pressure is controlled to be approximately from 0.01 to 10 Torr. Under such conditions, an inert gas may be introduced into the reaction vessel 1. In carrying out this reaction, the discharge output may be set to not more than 300 W. and preferably not more than 100 W. The coating formed on the lens substrate S may have a thickness usually from 50 to 2,000 Å, and preferably from 50 to 3,000 Å, in approximation. The polymerization can be completed usually in 10 minutes or less.

In the apparatus of a non-electrode type as illustrated in FIG. 2, a coil electrode 11 is provided on one end of a reaction vessel !0, and the inside of the reaction vessel is evacuated from an exhaust vent 12 to which a vacuum pump is connected from the side opposite to the coil electrode 11. Then an inert carrier gas as exemplified by argon and helium is fed from a carrier gas feed pipe 13 and an electric current is flowed to the coil electrode 11, thereby generating plasma. This plasma activates in the reaction vessel the monomers fed from the feed pipe 14, and thus a coating is formed on the lens substrate S. The carrier gas is introduced into a reaction vessel 10 so that the dissociation of the monomer gas can be suppressed. The energy source for the generation of plasma may be of either direct current or alternate current. The state in which the lens substrate S is set may be changed (for example, the lens may be reversed) so that the whole surface of the substrate S can be uniformly provided with the coating layer.

Figure 3:
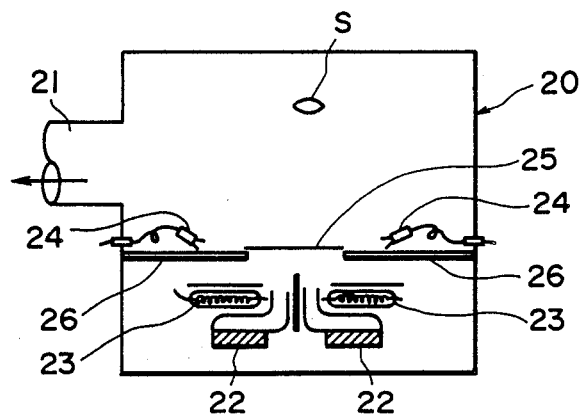
FIG. 3 is a side elevation of a vacuum desposition polymerization apparatus used in preparing the intraocular implant of the present invention.

A typical example for carrying out the vacuum deposition polymerization in the present invention by using the vacuum deposition polymerization apparatus as illustrated in FIG. 3 will be described below but by no means limited to this. In the case of this vacuum deposition polymerization apparatus, the inside of the reaction vessel 20 is evacuated from an exhaust vent 21. Monomer containers 22 in which monomers are put are heated with halogen lamps 23 to vaporize the monomers, thereby forming a coating on the lens substrate S. The thickness of the coating can be controlled by monitoring it using a monitor 24 to open or shut a shutter 25. The numeral 26 denotes a partition wall.

In this instance, for example, the inside of the reaction vessel 20 is evacuated to a vacuum of not more than $5 \times 10^{-4}$ Torr, and monomers are heated to a temperature at which they are sufficiently vaporized in the reaction vessel 20. The film formation is carried out while opening or shutting the shutter 25. The coating formed on the surface of the substrate lens 20 may have a thickness of from 50 to 20,000 Å, and preferably from 50 to 3,000 Å, in approximation, which can be formed usually within several ten minutes. A heat treatment may also be carried out after the coating has been formed, but it must be applied in the extent that the lens substrate S may not be affected adversely.

The lens substrate used in the present invention comprises PMMA, HEMA, silicone rubber, or &he like as previously described, and &he lens substrates made of these have a compatibility with organisms Which is preferable as the intraocular implant. These lens substrates may also be subjected to any desired treatment before the coating is formed thereon, without causing any difficulties. Such a treatment include, for example, an argon plasma treatment.

EXAMPLES

The effect of the present invention will become apparent from Examples set out below, but the scope of a right on the present invention is by no means limited to these Examples.

EXAMPLE 1

A PMMA lens With a thickness of 1 mm at maximum and a diameter of 7 mm was set as the lens substrate S in the plasma polymerization apparatus as illustrated in FIG. 1. The inside of the reaction vessel 1 was evacuated to a vacuum of $1 \times 10^{-6}$ Torr, and thereafter, while allylamine was fed from the monomer feed pipe 6 at a rate of 10 cc per minute, the pressure inside the reaction vessel 1 was controlled to be $1 \times 10^{-1}$ Torr. Then, While the temperature of the lens substrate S was maintained at 30° C., a high frequency electric power of 13.56 MHz was applied to the electrode 2b. The discharge output was 70 W, under which the plasma polymerization was carried out for 10 minutes. As a result, there was obtained an intraocular implant having on its surface a coating layer with a thickness of 1,000 Å.

The hydrophilic nature of the resulting intraocular implant was determined by measuring a contact angle to water using a dropping method for every prescribed days lapsed. On this intraocular implant, also measured Was transmittance of light with wavelengths of from 250 to 850 nm to determine the transmittances of visible light and ultraviolet light. The measurement results are shown in Tables 1 and 2.

Example 2

A silicone resin lens with a thickness of 1 mm at maximum and a diameter of 7 mm was set as the lens substrate S in the plasma polymerization apparatus as illustrated in FIG. 2. The inside of the reaction vessel 1 was evacuated to a vacuum of $1 \times 10^{-6}$ Torr, and thereafter, while argon gas was fed from the carrier gas feed pipe 13 at a rate of 10 SCCM per minute and acetonitrile monomers were fed from the monomer feed pipe 6 at a rate of 10 cc per minute, the pressure inside the reaction vessel 10 was controlled to be $2 \times 10^{-1}$ Torr. A high frequency electric power of 13.56 MHz was applied to the coil electrodes 11 to generate plasma. The discharge output was 50 W, under which the plasma polymerization was carried out for 10 minutes. As a result, there was obtained an intraocular implant having on its surface a coating layer with a thickness of 1,000 Å.

On the resulting intraocular implant the contact angle and transmittance were measured in the same manner as Example 1. The measurement results are shown in Tables 1 and 2.

EXAMPLE 3

In the same manner as Example 2, plasma polymerization was carried out using azoethane as monomers, to prepare an intraocular implant. Polymerization conditions and lens substrate were the same as used in Example 2. The contact angle and transmittance were measured to obtain the results as shown in Tables 1 and 2.

EXAMPLE 4

In the same manner as Example 2, plasma polymerization was carried out using glycine as monomers, to prepare an intraocular implant. Polymerization conditions and lens substrate were the same as used in Example 2. The contact angle and transmittance were measured to obtain the results as shown in Tables 1 and 2.

EXAMPLE 5

In the same manner as Example 1, plasma polymerization was carried out using an HEMA lens with a thickness of 1 mm in thickness at maximum and a diameter of 7 mm as the lens substrate S and also using allylamine as monomers, to prepare an intraocular implant. Polymerization conditions were the same as used in Example 1. The contact angle and transmittance were measured to obtain the results as shown in Tables 1 and 2.

EXAMPLE 6

A PMMA lens with a thickness of 1 mm at maximum and a diameter of 7 mm was set as the lens substrate S in the vacuum deposition polymerization apparatus as illustrated in FIG. 3. The inside of the reaction vessel I was evacuated to a vacuum of $5 \times 10^{-6}$ Torr, allylamine monomers in &he monomer containers 22 were heated to 200° C. to evaporate them, and the shutter 25 was kept open for 5 minutes, thus prepared an intraocular implant having on its surface a coating layer. The contact angle and transmittance of this intraocular implant were measured to obtain the results as shown in Tables 1 and 2.

EXAMPLE 7

In the same manner as Example 6, vacuum deposition polymerization was carried out using a silicone rubber lens with a thickness of 1 mm in thickness at maximum and a diameter of 7 mm as the lens substrate S, to prepare an intraocular implant. Polymerization conditions and lens substrate were the same as used in Example 6. The contact angle and transmittance were measured to obtain the results as shown in Tables 1 and 2.

COMPARATIVE EXAMPLE 1

In the same manner as Example 1, plasma polymerization was carried out using nitroethane as monomers, to prepare an intraocular implant. The polymerization conditions and lens substrate were the same as used in Example 1. The contact angle and transmittance were measured to obtain the results as shown in Tables 1 and 2.

COMPARATIVE EXAMPLE 2

In the same manner as Example 1, plasma polymerization was carried out using nitroethane as monomers, to prepare an intraocular implant. The polymerization conditions and lens substrate were the same as used in Example 2. The contact angle and transmittance were measured to obtain the results as shown in Tables 1 and 2.

COMPARATIVE EXAMPLE 3

A PMMA lens with a thickness of 1 mm at maximum and a diameter of 7 mm was set as the lens substrate S in the plasma polymerization apparatus as illustrated in FIG. 1. The inside of the reaction vessel 1 was evacuated to a vacuum of $1 \times 10^{-6}$ Torr, and thereafter, while nitrogen gas was fed from the carrier gas feed pipe 6 at a rate of 10 cc per minute, the pressure inside the reaction vessel 1 was controlled to be $3 \times 10^{-1}$ Torr. While maintaining the substrate temperature at 30° C., a high frequency electric power of 13.56 MHz was applied to the coil electrodes 11 to generate plasma. The discharge output was 50 W, under which the plasma polymerization was carrier out for 2 minutes, thus obtained an intraocular implant having on its surface a coating layer.

For the resulting intraocular implant, the contact angle and transmittance were measured to obtain the results as shown in Tables 1 and 2.

COMPARATIVE EXAMPLE 4

In the same manner as Comparative Example 3, plasma treatment was carried out using a silicone resin lens with a thickness of 1 mm in thickness at maximum and a diameter of 7 mm as the lens substrate S, to prepare an intraocular implant. Discharge conditions and gases were the same as used in Comparative Example 3. The contact angle and transmittance were measured to obtain the results as shown in Tables 1 and 2.

COMPARATIVE EXAMPLE 5

Contact angle and transmittance of a control silicone rubber substrate (with a thickness of 1 mm in thickness at maximum and a diameter of 7 mm) were measured. The measurement results are shown in Tables 1 and 2.

COMPARATIVE EXAMPLE 6

Contact angle and transmittance of a PMMA substrate (with a thickness of 1 mm in thickness at maximum and a diameter of 7 mm) were measured. The measurement results are shown in Tables 1 and 2.

EXAMPLE 8

Using allylamine as monomers, a coating layer was uniformly formed in the same manner as Example 2 on the whole surface of a substrate comprising silicone resin having a diameter of 10 mm and a thickness of 0.3 mm, thus prepared a sample. On this sample, water was dropped and a rubbing test was carried out by backward and forward rubbing it 10 times with tissue paper for lens under application of a load of 10 g. A similar rubbing test was also carried out using isopropyl alcohol (IPA).

COMPARATIVE EXAMPLE 7

The same test as Example 8 was carried out for a control silicone resin substrate having a diameter of 10 mm and a thickness of 0.3 mm.

The test results in these Example 8 and Comparative Example 7 are shown in Table 3, in which the sample having caused clouding is evaluated as "O", and the one having caused no clouding, as "X".

TABLE 1

| Days lapsed: | Contact angle ($\theta°$) | | | | | | |
|---|---|---|---|---|---|---|---|
| | 0 | 2 | 5 | 10 | 30 | 100 | 200 |
| Example 1 | 32 | 34 | 35 | 36 | 36 | 36 | 36 |
| Example 2 | 48 | 50 | 51 | 52 | 52 | 52 | 52 |
| Example 3 | 45 | 48 | 50 | 51 | 51 | 51 | 51 |
| Example 4 | 47 | 50 | 51 | 52 | 52 | 52 | 52 |
| Example 5 | 38 | 41 | 42 | 42 | 42 | 42 | 42 |
| Example 6 | 32 | 35 | 37 | 38 | 38 | 38 | 38 |
| Example 7 | 35 | 38 | 41 | 42 | 43 | 43 | 43 |
| Comparative Example 1 | Coating dissolved in water | | | | | | |
| Comparative Example 2 | Coating dissolved in water | | | | | | |
| Example 3 | 40 | 64 | 65 | 65 | 65 | 65 | 65 |
| Example 4 | 40 | 120 | 120 | 120 | 120 | 120 | 120 |
| Example 5 | 120 | 120 | 120 | 120 | 120 | 120 | 120 |
| Example 6 | 65 | 65 | 65 | 65 | 65 | 65 | 65 |

TABLE 2

| Wavelength: (nm) | Transmittance (%) | | | | | | |
|---|---|---|---|---|---|---|---|
| | 850 | 600 | 450 | 400 | 350 | 300 | 250 |
| Example 1 | 91 | 90 | 85 | 80 | 70 | 6 | 5 |
| Example 2 | 92 | 92 | 90 | 78 | 69 | 42 | 22 |
| Example 3 | 91 | 91 | 90 | 76 | 58 | 40 | 21 |
| Example 4 | 92 | 92 | 90 | 77 | 59 | 44 | 30 |
| Example 5 | 92 | 92 | 87 | 80 | 68 | 52 | 5 |
| Example 6 | 90 | 90 | 90 | 86 | 55 | 15 | 5 |
| Example 7 | 91 | 91 | 91 | 90 | 84 | 40 | 14 |
| Comparative Example 1 | 90 | 90 | 90 | 90 | 90 | 80 | 5 |
| Comparative Example 2 | 92 | 92 | 92 | 92 | 92 | 82 | 72 |
| Comparative Example 3 | 92 | 92 | 92 | 92 | 92 | 85 | 5 |
| Comparative Example 4 | 94 | 94 | 93 | 93 | 92 | 90 | 80 |
| Comparative Example 5 | 94 | 94 | 93 | 93 | 92 | 90 | 80 |
| Comparative Example 6 | 92 | 92 | 92 | 92 | 92 | 85 | 5 |

TABLE 3

|  | Water | IPA |
|---|---|---|
| Example 8 |  |  |
| Comparative Example 7 |  | X |

As described in the above, the intraocular implant of the present invention has the following advantages.

(1) A stable hydrophilic nature free of deterioration with time can be attained.

(2) The hydrophilic nature and ultraviolet light screening properties can be concurrently attained without any lowering of mechanical strength of lenses.

(3) Because of a higher cross-link degree and better barrier properties of the coating layer as compared with the substrate, it does not occur that the free monomers in the lens substrate dissolve into an eye.

We claim:

1. An intraocular implant, comprising a lens substrate having on the surface thereof a coating layer, wherein said coating layer is comprised of at least one compound selected from the group consisting of;

an amino compound represented by the general formula: $R_1$-$NH_2$, wherein $R_1$ represents a hydrocarbon group having not more than 10 carbon atoms;

a cyan compound represented by the general formula: $R_2$-CN, wherein $R_2$ represents a hydrocarbon group having not more than 10 carbon atoms;

an azo compound represented by the general formula: $R_3$-N=N-$R_4$, wherein $R_3$ and $R_4$ represent hydrocarbon groups having not more than 10 carbon atoms in total or hydrogen atoms: and an amino acid represented by the general formula: $R_5$-CH($NH_2$)COOH, wherein $R_5$ represents a substituent constituted of C, H or N.

2. The intraocular implant according to claim 1, wherein said lens substrate comprises a material selected from the group consisting of polymethyl methacrylate, hydroxyethyl methacrylate, a silicone resin and a polyurethane resin.

3. The intraocular implant according to claim 1, wherein said coating layer is formed by plasma polymerization.

4. The intraocular implant according to claim 1, wherein said coating layer is formed by vacuum deposition polymerization.

5. The intraocular implant according to claim 1, wherein said coating layer has a thickness of from 50 to 20,000 Å.

6. The intraocular implant according to claim 5, wherein said coating layer has a thickness of from 50 to 3,000 Å.

* * * * *

UNITED STATES PATENT AND TRADEMARK OFFICE
CERTIFICATE OF CORRECTION

PATENT NO. : 4,955,901

DATED : September 11, 1990

INVENTOR(S) : TOSHIJI NISHIGUCHI, ET AL.

It is certified that error appears in the above-identified patent and that said Letters Patent is hereby corrected as shown below:

COLUMN 1

Line 36, "&he" should read --the--.
Line 45, "treatment&" should read --treatment--.
Line 53, "an" should read --a--.
Line 55, "water soluble" should read --water-soluble--.
Line 56, "a such w" should read --a narrower scope. The film formation carried out at such a--.
Line 58, "narrower scope. The film formation" should be deleted.
Line 59, "carried out at" should be deleted.

COLUMN 2

Line 5, "However" should read --However,-- and "ultraviolet absorbing" should read --ultraviolet-absorbing--.
Line 13, "laYer" should read --layer--.
Line 22, "of;" should read --of:--.
Line 57, "knoWn" should read --known--.

COLUMN 3

Line 9, "With" should read --with--.
Line 12, "$R_1$-$NH_2$includes" should read --$R_1$-$NH_2$ includes--.
Line 28, "2-aminop-xylene," should read --2-amino-p-xylene,--.
Line 49, "thalene. formula:" should read --thalene. ¶ The azo compound represented by the general formula:--.
Line 55, "methneazoethylene, methneazopropylene" should read --methaneazoethylene, methaneazopropylene--.

UNITED STATES PATENT AND TRADEMARK OFFICE
CERTIFICATE OF CORRECTION

PATENT NO.  : 4,955,901
DATED       : September 11, 1990
INVENTOR(S) : TOSHIJI NISHIGUCHI, ET AL.

It is certified that error appears in the above-identified patent and that said Letters Patent is hereby corrected as shown below:

COLUMN 4

Line 33, "opposed" should read --opposed to--.
    Line 44, "Which" should read --which--.
    Line 65, "vessel !0," should read --vessel 10,--.

COLUMN 5

Line 15, "sitIon" should read --sition--.
    Line 17, "descrIbed below but" should read --described below, but is--.
    Line 41, "&he" should read --the--.
    Line 42, "&he" should read --the--.
    Line 43, "Which" should read --which--.
    Line 47, "include," should read --includes,--.
    Line 57, "With" should read --with--.
    Line 65, "While" should read --while--.

COLUMN 6

Line 8, "Was" should read --was--.
    Line 13, "Example 2" should read --EXAMPLE 2--.
    Line 30, "implant the" should read --implant, the--.
    Line 68, "&he" should read --the--.

COLUMN 7

Line 2, "prepared" should read --preparing--.
    Line 49, "carrier" should read --carried-- and "obtained" should read --was obtained--.

UNITED STATES PATENT AND TRADEMARK OFFICE
CERTIFICATE OF CORRECTION

PATENT NO. : 4,955,901

DATED : September 11, 1990

INVENTOR(S) : TOSHIJI NISHIGUCHI, ET AL.

It is certified that error appears in the above-identified patent and that said Letters Patent is hereby corrected as shown below:

COLUMN 8

Line 15, "prepared" should read --preparing--.

COLUMN 9

TABLE 3, "Example 8
      Comparative Example 7         X"

should read

--Example 8                   O    O
       Comparative Example 7    O    X--.

Line 24, "of;" should read --of:--.

Signed and Sealed this

Eighth Day of September, 1992

Attest:

DOUGLAS B. COMER

Attesting Officer        Acting Commissioner of Patents and Trademarks